United States Patent
Liu et al.

(10) Patent No.: US 10,107,778 B2
(45) Date of Patent: Oct. 23, 2018

(54) SYSTEM AND METHOD FOR DETECTING LYSYL OXIDASE-LIKE 2 PROTEIN (LOXL2) AND BREAST CANCER

(71) Applicant: Case Western Reserve University, Cleveland, OH (US)

(72) Inventors: Chung-Chiun Liu, Cleveland, OH (US); Yuan Zhang, Cleveland, OH (US); Metini Janyasupab, Cleveland, OH (US); Cheng-Wei Liu, Cleveland, OH (US); Laurie Dudik, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 336 days.

(21) Appl. No.: 14/427,904

(22) PCT Filed: Sep. 30, 2013

(86) PCT No.: PCT/US2013/062628
§ 371 (c)(1),
(2) Date: Mar. 12, 2015

(87) PCT Pub. No.: WO2014/052962
PCT Pub. Date: Apr. 3, 2014

(65) Prior Publication Data
US 2015/0253280 A1    Sep. 10, 2015

Related U.S. Application Data

(60) Provisional application No. 61/706,944, filed on Sep. 28, 2012.

(51) Int. Cl.
| | |
|---|---|
| *G01N 27/327* | (2006.01) |
| *C12Q 1/26* | (2006.01) |
| *G01N 33/574* | (2006.01) |
| *A61B 10/00* | (2006.01) |
| *A61B 5/15* | (2006.01) |

(52) U.S. Cl.
CPC ....... *G01N 27/3277* (2013.01); *A61B 10/007* (2013.01); *C12Q 1/26* (2013.01); *G01N 27/3278* (2013.01); *G01N 33/57415* (2013.01); *A61B 5/150755* (2013.01); *G01N 2333/90638* (2013.01); *G01N 2800/365* (2013.01); *G01N 2800/7028* (2013.01)

(58) Field of Classification Search
CPC ....................................................... C12Q 1/26
See application file for complete search history.

(56) References Cited

U.S. PATENT DOCUMENTS

| | | |
|---|---|---|
| 2010/0209415 A1 | 8/2010 | Smith et al. |
| 2011/0076739 A1 | 3/2011 | McCauley et al. |
| 2011/0200606 A1 | 8/2011 | McCauley et al. |

FOREIGN PATENT DOCUMENTS

| | | |
|---|---|---|
| WO | 2009035791 A1 | 3/2009 |
| WO | 2011022670 A1 | 2/2011 |

OTHER PUBLICATIONS

Janyasupab et al. J of Nanotechnology, 2011, pp. 1-6.*
Chen, Kuan-Jung, et al., "Bimetallic PtM (M=Pd, Ir) nanoparticle decorated multi-walled carbon nanotube enzyme-free, mediator-less amperometric snesor for H2O2", Biosensors and Bioelectronics, vol. 33, No. 1, Mar. 1, 2012.
Lin, Po-Yuan, et al., "Detection of Alpha-Methylacyl-CoA Racemase (AMACR), a Biomarker of prostate Cancer, in Patient Blood Samples Using Nanoparticle Electrochemical Biosensor", Biosensor MDPAAG, CH, vol. 2, No. 4, Sep. 26, 2012.
Janyasupab, Metini, "New Designs of Electrochemical H2O2 Based Biosensors for Advanced Medical Diagnosis", PhD Thesis, May 1, 2013, pp. 1-114.
Kirschmann, et al. "A Molecular Role for Lysyl Oxidase in Breast Cancer Invasion", Cancer Research, 62(15), 2002, 4478-4483.
Chinese Office Action dated Sep. 2, 2016.
Supplementary European Search Report, dated Jun. 15, 2015.
European Action dated Apr. 22, 2016.
Office Action for Chinese Application No. 201380051094.9, dated Jan. 23, 2017.
Herranz, et al., "Lysyl oxidase-like 2 deaminates lysine 4 in histone H3", Molecular Cell. vol. 46, Issue 3, pp. 36-376, May 11, 2012.
Office action for European Patent Application No. 13 840 525.3-1408, dated Nov. 6, 2017.

* cited by examiner

*Primary Examiner* — Bin Shen
(74) *Attorney, Agent, or Firm* — Tarolli, Sundheim, Covell & Tummino LLP (57) ABSTRACT

A detection system for determining lysyl oxidase-like 2 protein (LOXL2) levels in a bodily sample, includes at least one reaction solution for generating $H_2O_2$ upon combination with LOXL2 in the bodily sample, the reaction solution including lysine that can be oxidatively deaminated by LOXL2 to generate α-aminoadipic-δ-semialdehyde (allysine) and hydrogen peroxide ($H_2O_2$).

12 Claims, 6 Drawing Sheets

SYSTEM AND METHOD FOR DETECTING LYSYL OXIDASE-LIKE 2 PROTEIN (LOXL2) AND BREAST CANCER

RELATED APPLICATION

This application claims priority from U.S. Provisional Application No. 61/706,944, filed Sep. 28, 2012, the subject matter of which is incorporated herein by reference in its entirety.

BACKGROUND

Breast cancer is a significant health concern in the United States, representing the second leading cause of cancer death in women. The lethality of breast cancers reflects their acquisition of invasive and metastatic phenotypes, events that account for nearly 90% of the mortality associated with mammary carcinomas. While the 5-year survival rate for women diagnosed with localized disease is high at 98%, this rate drops abruptly to 23% for women who exhibit evidence of metastasis at the time of diagnosis. At present, the molecular mechanisms that underlie the development and initiation of metastasis remain incompletely understood, as does the means to effectively monitor patients for disease progression. Along these lines, breast cancer cells often disseminate in patients with small mammary tumors (<4 mm) and prior to the point where the disease becomes symptomatic. Similarly, disseminated breast cancer cells often escape clinical detection by acquiring dormant phenotypes, only to reemerge later as aggressive recurrent tumors that no longer respond to the therapeutic regimens used in treating the original tumor.

Breast cancer is not a homogenous disease, but is instead a heterogeneous disease comprised of at least 5 genetically distinct subtypes that exhibit disparate (i) histopathological features, grades, and markers; (ii) clinical presentations, prognoses, and outcomes; and (iii) responses to chemotherapies. Collectively, these challenges highlight the need to develop novel diagnostic platforms capable of detecting breast cancers in otherwise seemingly healthy women.

Amongst individual breast cancer subtypes, those classified as triple-negative breast cancers (TNBCs) are especially lethal due to their highly aggressive and metastatic behavior, and to their propensity to recur following apparent remission. TNBCs lacked expression of hormone receptors (estrogen and progesterone) and ErbB2/HER2. However, they typically possess BRCA1- and p53-defects and/or -deficiencies. This unique phenotype prevented the development of targeted chemotherapies effectively against TNBCs, which also possess a heightened propensity to acquire resistance to standard-of-care chemotherapeutic agents (e.g., doxorubicin, cisplatin, and taxanes). Moreover, the diagnosis of TNBC is one of exclusion, not one of inclusion because specific biomarkers for this disease did not exist. Recently, several serum biomarkers for breast cancer were employed in clinical settings. This limited list included the cancer antigens (CA): CA15-3, CA27.29, and carcinoembryonic antigen (CEA), and all lacked the needed sensitivity and specificity.

Recent findings linked the aberrant expression of LOXL2 to breast cancer metastasis and disease progression, particularly in patients harboring late-stage and poorly differentiated TNBCs (Peinado, H.; Portillo, F.; Cano, A. Switching On-Off Snail: LOXL2 Versus GSK3? *Cell Cycle* 4, 1749 (2005); Peinado, H. et al., Lysyl Oxidase-Like 2 as a New Poor Prognosis Marker of Squamous Cell Carcinomas. *Cancer Research* 68, 4541 (Jun. 15, 2008, 2008); Kagan, H. M.; Li, W. Lysyl oxidase: Properties, specificity, and biological roles inside and outside of the cell. *Journal of Cellular Biochemistry* 88, 660 (2003); and Lucero, H. A.; Kagan, H. M. Lysyl oxidase: an oxidative enzyme and effector of cell function. *Cell Mol Life Sci* 63, 2304 (October, 2006)). Similarly, dysregulated LOXL2 expression predicts for disease recurrence and poor prognosis in breast cancer patients (Erler, J. T.; Giaccia, A. J. Lysyl oxidase mediates hypoxic control of metastasis. *Cancer Res* 66, 10238 (Nov. 1, 2006); Payne, S. L.; Hendrix, M. J.; Kirschmann, D. A. Paradoxical roles for lysyl oxidases in cancer—a prospect. *J Cell Biochem* 101, 1338 (Aug. 15, 2007); Nishioka, T.; Eustace, A.; West, C. Lysyl oxidase: from basic science to future cancer treatment. *Cell Struct Funct* 37, 75 (2012); Taylor, M. A. Amin, J.; Kirschmann, D. A.; Schiemann, W. P. Lysyl oxidase contributes to mechanotransduction J-mediated regulation of transforming growth factor-β signaling in breast cancer cells. *Neoplasia* 13, 406 (2011) and Barker, H. E.; Erler, J. E. The potential for LOXL2 as a target for future cancer treatment. *Future Oncol* 7, 707 (June, 2011).).

SUMMARY

Embodiments described herein relate to a detection system for determining lysyl oxidase-like 2 protein (LOXL2) levels in a bodily sample and/or detection of breast cancer in a subject. The detection system includes at least one reaction solution for generating $H_2O_2$ upon combination with LOXL2 in the bodily sample and a biosensor for determining the level of the generated $H_2O_2$. In some embodiments, the at least one reaction solution includes lysine that can be oxidatively deaminated by LOXL2 to generate α-aminoadipic-δ-semialdehyde (allysine) and hydrogen peroxide ($H_2O_2$).

In some embodiments, the bodily sample can include a bodily fluid selected from the group consisting of blood, plasma, sera, and urine.

In other embodiments, the biosensor can include a working electrode and a counter electrode. The working electrode and counter electrode can include catalyst particles that can increase the rate of electrochemical oxidation-reduction reaction with $H_2O_2$ and provide the detection of $H_2O_2$ at a lower oxidation potential than without the presence of the catalyst particles. The catalyst particles can include nanoparticle metallic catalysts, such as a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, the catalyst particles can comprise iridium oxide particles.

The detection system can also include a measuring device for applying a voltage potential to the working electrode and measuring the current flow between the working electrode and counter electrode.

Other embodiments relate to a method of detecting LOXL2 levels in a bodily fluid as well as detecting breast cancer or an increased risk of breast cancer in a subject. The method includes obtaining a bodily sample from the subject. The bodily sample includes a bodily fluid selected from the group consisting of blood, plasma, sera, and urine. The bodily sample is combined with at least one reaction solution for generating $H_2O_2$ upon combination with LOXL2 in the bodily sample. In some embodiments, the at least one reaction solution includes lysine that can be oxidatively deaminated by LOXL2 to generate α-aminoadipic-δ-semi-aldehyde (allysine) and hydrogen peroxide ($H_2O_2$). The amount of $H_2O_2$ generated in the reaction solution is detected with a biosensor. An increased amount of $H_2O_2$ detected compared to a control is indicative of an increased amount level of LOXL2 in the bodily sample as well as indicative of the subject having breast cancer or an increase risk of breast cancer.

In some embodiments, the biosensor can include a working electrode and a counter electrode. The working electrode and counter electrode can include catalyst particles that can increase the rate of electrochemical oxidation-reduction reaction with $H_2O_2$ and provide the detection of $H_2O_2$ at a lower oxidation potential than without the presence of the catalyst particles. The catalyst particles can include nanoparticle metallic catalysts, such as a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, the catalyst particles can comprise iridium oxide particles.

BRIEF DESCRIPTION OF THE DRAWINGS

FIGS. 3(A-B) illustrates plots showing cyclic voltammograms using a LOXL2 biosensor in accordance with an aspect of the application of (A) CV curves measured during the in situ generation of allysine recorded at different time intervals. (B) CV curves obtained from different concentrations of $NH_3^-H_2O$.

FIGS. 5 (A-C) illustrate plots showing the detection of LOXL2 activity in murine and human biological fluids. (A) The application of whole-blood samples to the LOXL2 biosensor clearly delineates tumor-free mice from those harboring mammary tumors. Data are the mean±SD (n=3). (B and C) The LOXL2 biosensor readily detects LOXL2 activity in serum (B) and (C) collected from normal controls and breast cancer patients. Data are the mean±SD (n=3).

DETAILED DESCRIPTION

Unless specifically addressed herein, all terms used have the same meaning as would be understood by those of skilled in the art of the present invention. The following definitions will provide clarity with respect to the terms used in the specification and claims to describe the present invention.

The term "monitoring" as used herein refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, diagnosis of an initial stage of disease recurrence in patients with seemingly stable remission, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

The term "quantitative data" or "quantitative level" or "quantitative amount" as used herein refers to data, levels, or amounts associated with any dataset components (e.g., markers, clinical indicia,) that can be assigned a numerical value.

The term "subject" as used herein refers to a human, or another mammal, that can be afflicted by a neoplastic disease, including breast cancer, but may or may not have such a disease. Typically, the terms "subject" and "patient" are used herein interchangeably in reference to a human individual.

As used herein, the term "subject suspected of having breast cancer" refers to a subject that presents one or more symptoms indicative of breast cancer or that is being screened for breast cancer (e.g., during a routine physical examination and/or mammogram). A subject suspected of having breast cancer may also have one or more risk factors. The term encompasses individuals who have not been tested for breast cancer, individuals who have received an initial diagnosis (e.g., a positive mammogram, a positive ultrasound and/or a positive CT scan showing a mass and/or microcalcifications) but for whom the stage of cancer is not known, as well as individuals for whom the stage and/or grade of cancer has been determined by a conventional method (e.g., fine needle aspirate and cytological analysis and/or surgical biopsy and histopathological analysis). The term also includes patients who have previously undergone therapy for breast cancer, including lumpectomy, mastectomy and radiation therapy.

As used herein, the term "subject at risk for breast cancer" refers to a subject with one or more risk factors for developing breast cancer. Risk factors include, but are not limited to age, sex, genetic predisposition, previous incidents with cancer, pre-existing non-cancer diseases, increased estrogen exposure, and dietary and environmental factors.

The term "diagnosing breast cancer" as used herein refers to a process aimed at one or more of: determining if a subject is afflicted with breast cancer; determining the severity or stage of breast cancer in a subject; determining the risk that a subject is afflicted with breast cancer; and determining the prognosis of a subject afflicted with breast cancer.

As used herein, the term "subject diagnosed with breast disease" refers to a subject who has been tested and found to have breast disease. The diagnosis may be performed using any suitable method, including, but not limited to, x-ray (e g, mammogram) biopsy, fine needle aspirate, ultrasound, blood test, and the methods described herein.

The term "providing a prognosis" is used herein to mean providing information regarding the impact of the presence of breast cancer (e.g., as determined by the methods described herein) on a subject's future health. Providing a prognosis may include predicting one or more of: breast cancer progression, the likelihood of breast cancer-attributable death, the average life expectancy of the patient, the likelihood that the patient will survive for a given amount of time (e.g., 6 months, 1 year, 5 years, etc), the likelihood that the patient will be disease-free for a specified prolonged period of time, the likelihood of getting breast cancer, the likelihood of developing aggressive breast cancer, the likelihood of recurrence, and the risk of metastasis. In certain embodiments, the prognosis methods of the invention are used clinically to make treatment decisions by choosing the most appropriate treatment modalities for any particular patient.

The term "bodily sample" is used herein in its broadest sense. A bodily sample may be obtained from a subject (e.g., a human) or from components (e.g., tissues) of a subject. The sample may be of any biological tissue or fluid with which biomarkers described herein may be assayed. Frequently, the sample will be a "clinical sample", i.e., a sample derived from a patient. Such samples include, but are not limited to, bodily fluids, e.g., urine, blood, plasma, or sera; and archival samples with known diagnosis, treatment and/ or outcome history. The term biological sample also encompasses any material derived by processing the biological sample. Processing of the bodily sample may involve one or more of, filtration, distillation, extraction, concentration, inactivation of interfering components, addition of reagents, and the like.

The terms "normal" and "healthy" are used herein interchangeably. They refer to an individual or group of individuals who have not shown any symptoms of breast cancer, and have not been diagnosed with breast cancer. Preferably, the normal individual (or group of individuals) is not on medication affecting breast cancer. In certain embodiments, normal individuals have similar sex, age, body mass index as compared with the individual from which the sample to be tested was obtained. The term "normal" is also used herein to qualify a sample isolated from a healthy individual.

The terms "control" or "control sample" as used herein refer to one or more biological samples isolated from an individual or group of individuals that are normal (i.e., healthy). The term "control", "control value" or "control sample" can also refer to the compilation of data derived from samples of one or more individuals classified as normal, and/or one or more individuals diagnosed with breast cancer or diagnosed with a particular sub-type or stage of breast cancer.

The term "indicative of breast cancer" as used herein, when applied to an amount of LOXL2 in a bodily sample, refers to a level or an amount, which is diagnostic of breast cancer such that the level is found significantly more often in subjects with the disease than in patients without the disease or another stage of breast cancer (as determined using routine statistical methods setting confidence levels at a minimum of 95%). Preferably, a level, which is indicative of breast cancer, is found in at least about 60% of patients who have the disease and is found in less than about 10% of subjects who do not have the disease. More preferably, a level, which is indicative of prostate cancer, is found in at least about 70%, at least about 75%, at least about 80%, at least about 85%, at least about 90%, at least about 95% or more in patients who have the disease and is found in less than about 10%, less than about 8%, less than about 5%, less than about 2.5%, or less than about 1% of subjects who do not have the disease.

Embodiments described herein relate to a detection system and in vitro assay or method for detecting, identifying, quantifying, and/or determining the level of lysyl oxidase-like 2 protein (LOXL2) in a bodily sample to diagnose, identify, stage, and/or monitor breast cancer in a subject having, suspected of having, or at risk of breast cancer. The detection system and method provides a single use, disposable, and cost-effective biosensor for simple point-of-care and early detection of breast cancer using bodily fluids, which minimizes complicated and painful clinical procedures for cancer screening.

In vitro assays for the detection of LOXL2, a protein that has been identified to correlate with the occurrence of breast cancer and the survival of breast cancer patients, have not yet been developed based on the biochemical pathway described herein. In this application, an in vitro assay is provided that can use electrocatalysts to enhance the sensitivity of an electrochemical biosensor that can screen bodily samples, such as bodily fluids, including blood, sera, plasma or urine samples, for the detection, diagnosis, identification, staging, and/or monitoring of breast cancer.

The detection system and assay or method described herein includes at least one reaction solution that can be used to generate a detectable and/or quantifiable analyte, which is indicative of the concentration or level of LOXL2 in a bodily fluid of a subject suspected of having or at risk of breast cancer, and a biosensor for detecting the analyte in the reaction solution. The components of the reaction solution are based on a biochemical pathway that necessitates the participation of LOXL2 in the mechanistic sequence, where none of the reactants or the products interferes with the current produced due to hydrogen peroxide ($H_2O_2$) production.

The reaction solution includes a LOXL2 substrate capable of biochemically reacting with LOXL2 to generate $H_2O_2$. A LOXL2 substrate can include a nonpeptidyl amine lysyl oxidase substrate and/or a peptidyl amine lysyl oxidase substrate. Non limiting examples of a LOXL2 substrate capable of biochemically reacting with LOXL2 to generate $H_2O_2$ include lysine (e.g., L-lysine), a peptidyl-lysine, and 1,5-diaminopentane (DAP). The amount, concentration, or level of $H_2O_2$ generated by the biochemical reaction of the reaction sample and LOXL2 in the bodily sample obtained from the subject suspected of having or at risk of breast cancer can be measured using the biosensor to determine the amount, concentration, or level of LOXL2 in the bodily sample and hence whether the subject has breast cancer or an increased risk of breast cancer.

In some aspects, the reaction solution includes lysine that can be oxidatively deaminated by LOXL2 in the bodily fluid to generate α-aminoadipic-δ-semialdehyde (allysine), $NH_3$ ($NH_4OH$ in aqueous solution) and an analyte, $H_2O_2$. The amount or quantity of $H_2O_2$ generated by biochemical reaction of the reaction fluid and LOXL2 in the bodily fluid obtained from the subject suspected of having or at risk of breast cancer can be measured using the biosensor to determine the level and quantity of LOXL2 in the bodily fluid and hence whether the subject has breast cancer or an increased risk of breast cancer.

In some embodiments, the at least one reaction solution includes L-lysine of which the δ-amino group can form a reaction substrate for LOXL2. The lysine can be, for example, a peptidyl-lysine. In one example, a peptidyl-lysine possessing a δ-amino group is oxidatively deaminated by LOXL2 to produce peptidyl-α-aminoadipic-δ-semialdehyde (allysine) in reaction scheme 1 shown below.

As shown in reaction scheme 1 above, peptidyl-lysine can react with a proper quantity of oxygen ($O_2$) and $H_2O$, which can also be provided in the reaction solution, forming allysine, $NH_3$ ($NH_4OH$ in aqueous solution) and $H_2O_2$, where the $H_2O_2$ may then be detected electrochemically.

The $H_2O_2$ produced due to peptidyl-lysine reaction with oxygen ($O_2$) and $H_2O$ in the presence of LOXL2 can be detected and quantified electrochemically and compared to a control value or level to determine the quantity of LOXL2 in a bodily sample. A sensor, which can measure the generated $H_2O_2$, quantitatively can be used to measure the stoichiometric quantity of the LOXL2. The quantity of LOXL2 in the bodily fluid obtained from a subject suspected of having or at risk of breast cancer can directly affect $H_2O_2$ production. The $H_2O_2$ generated can be quantified by the biosensor and in turn be used to quantify the level of LOXL2 in the bodily sample. The quantified level of $H_2O_2$ generated can be compared to a control or predetermined value to determine if or whether the subject has breast cancer. Thus, in some embodiments, the at least one reaction solution to which the bodily fluid obtained from the subject is added can include lysine and $H_2O$ in the presence of $O_2$.

By way of example, in preparing the reaction solution, 10 mg of lysine powder, purchased from Sigma-Aldrich (St. Louis, Mo.), was mixed with 1 mL of distilled water and subsequently diluted to a working concentration of 680 nM. 50 µl of this solution was then combined with 5 µl of a subject sample to form the reaction solution and incubated for 400 seconds. Then 10 µl of the incubated test solution is placed on top of the working electrode for measurement of the $H_2O_2$ generated. Advantageously, the reaction solution does not include any reagents or byproducts that would potentially contribute to background oxidation current of the biosensor and impair detection and quantification of the $H_2O_2$ generated.

The reaction solution so formed can be mixed with a bodily sample, such as a bodily fluid (e.g., blood, sera, plasma, or urine) obtained from the subject. In some aspects, the amount of blood taken from a subject is about 0.1 ml or more and the amount added to about 50 µl of the reaction solution can be about 5 µl or less. In an exemplary embodiment, the bodily sample is blood plasma isolated from a whole blood sample obtained from a subject. Blood plasma may be isolated from whole blood using well known methods, such as centrifugation. In another exemplary embodiment, the bodily sample is urine.

The bodily samples can be obtained from the subject using sampling devices, such as syringes, swabs or other sampling devices used to obtain liquid and/or solid bodily samples either invasively (i.e., directly from the subject) or non-invasively. These samples can then be stored in storage containers. The storage containers used to contain the collected sample can include a non-surface reactive material, such as polypropylene. The storage containers should generally not be made from untreated glass or other sample reactive material to prevent the sample from becoming absorbed or adsorbed by surfaces of the glass container.

Collected samples stored in the container may be stored under refrigeration temperature. For longer storage times, the collected sample can be frozen to retard decomposition and facilitate storage. For example, samples obtained from the subject can be stored in a falcon tube and cooled to a temperature of about −80°.

The $H_2O_2$, which is generated by addition of the bodily sample containing LOXL2 to the reaction solution, is an electrochemically active species that can be oxidized or reduced under appropriate conditions and detected using an $H_2O_2$ biosensor to quantify the level of LOXL2 in the biological fluid and determine whether the subject has or is at risk of breast cancer. The $H_2O_2$ biosensor can include a two or three electrode electrochemical biosensor. The biosensor can be manufactured by established micro-fabrication techniques, including thick film screen printing, ink jet printing, or laser etching processes. This fabrication process can also use a combination of these and any other fabrication techniques. This provides a cost-effective, single use, disposable biosensor minimizing any electrode cleaning, sterilization and electrode fouling problems.

Figure 1:
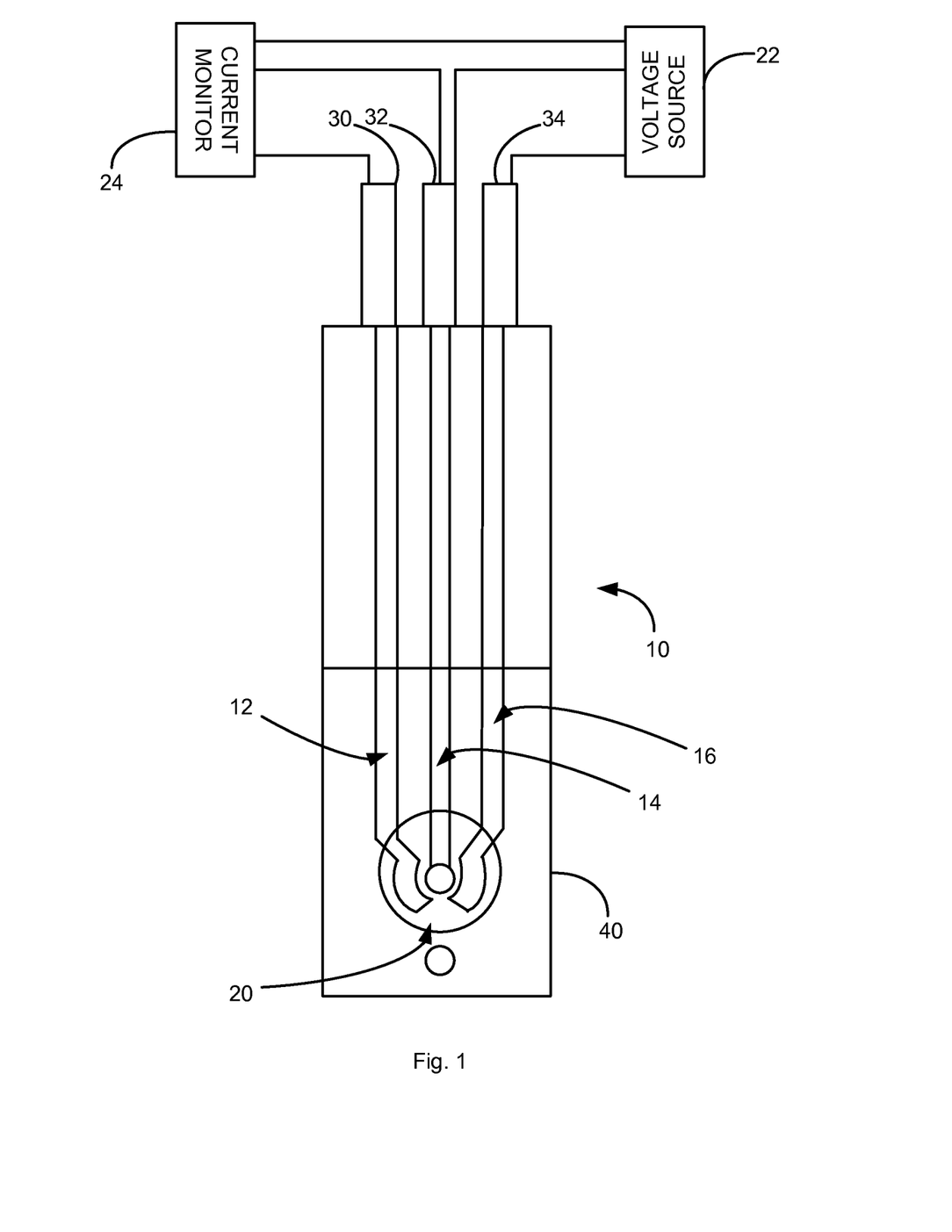
FIG. 1 is a schematic illustration of a biosensor in accordance with an aspect of the application.

FIG. 1 illustrates an $H_2O_2$ biosensor 10 in accordance with an embodiment of the application. The biosensor 10 is a three-electrode sensor including a counter electrode 12, a working electrode 14, and a reference electrode 16, which are exposed to the reaction solution in a detection region 20 of the biosensor 10. A voltage source 22 is connected to the working and reference electrodes 14, 16. A current measuring device 24 is connected to the working and counter electrodes 14, 12 to measure the current generated by the redox reaction of $H_2O_2$ when the mixture of reaction solution and biological sample is added to the detection region 20 of the biosensor 10.

The working electrode 14 is the site of the redox reaction of $H_2O_2$, and where the charge transfer occurs. The function of the counter electrode 12 is to complete the circuit, allowing charge to flow through the sensor 10. The working electrode 14 and the counter electrode 12 are preferably formed of the same material, although this is not a requirement. Examples of materials that can be used for the working electrode 14 and counter electrode 12 include, but are not limited to, gold, platinum, palladium, silver, and carbon.

Examples of materials that can be used to form the reference electrode 16 are silver-silver chloride and mercury-mercuric chloride (Calomel). Silver-silver chloride is preferred. The silver can be applied to a substrate in the form of a silver ink, which is commercially available, or can be made using finely dispersed metal particles, solvent, and a binder. Respective silver contact pads 30, 32, and 34 are connected with each of the electrodes 12, 14, and 16. An insulation layer 40 may cover part of the electrodes 12, 14, and 16, leaving tips of the electrodes 12, 14, and 16 exposed to the detection environment in the detection region 20.

In some embodiments, the working and counter electrodes 14, 12 can include a layer of particles, such as micro-, meso- or nano-sized particles of active carbon or porous carbon. The active carbon nanoparticles may be combined with metallic catalyst particles that increase the rate of electrochemical oxidation-reduction reaction with $H_2O_2$ and provide the detection of $H_2O_2$ at a lower oxidation potential than without the presence of the catalyst particles. In terms of the practical applications, the metallic catalyst particles can shorten the reaction time and lower the applied electrochemical potential for detection of $H_2O_2$ in the mixture of the reaction solution and biological sample. Lowering the applied potential often leads to the minimization of electrochemical oxidation or reduction of other species presented, resulting in a minimization of interference caused by the unwanted reaction of the confounding species. As a result, a highly specific biosensor can be obtained and produced.

The metallic catalyst particles can include nano-, meso-, or micro-scale particles of a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb. In one embodiment, for example, the metallic catalyst particles may be composed of a unary metal, unary metal oxide binary metal, or binary metal oxide, such as iridium, iridium oxide, platinum, ruthenium, platinum-ruthenium, platinum-nickel, and platinum-gold.

In one example, the working electrode 14 and the counter electrode 12 can be made of active carbon and include about 2 to about 5 weight percent iridium oxide nanoparticles. Incorporation of about 2 to about 5 weight percent iridium oxide nanoparticles into the working electrode and counter electrode can lower oxidation potential of $H_2O_2$ in the mixture of reaction solution and biological to 0.25 Volt versus a standard Ag/AgCl reference electrode from about 0.40 to about 0.45 Volt. At this lower potential, oxidation of other biological species in the mixture of the reaction solution and biological can be minimized.

Figure 2:
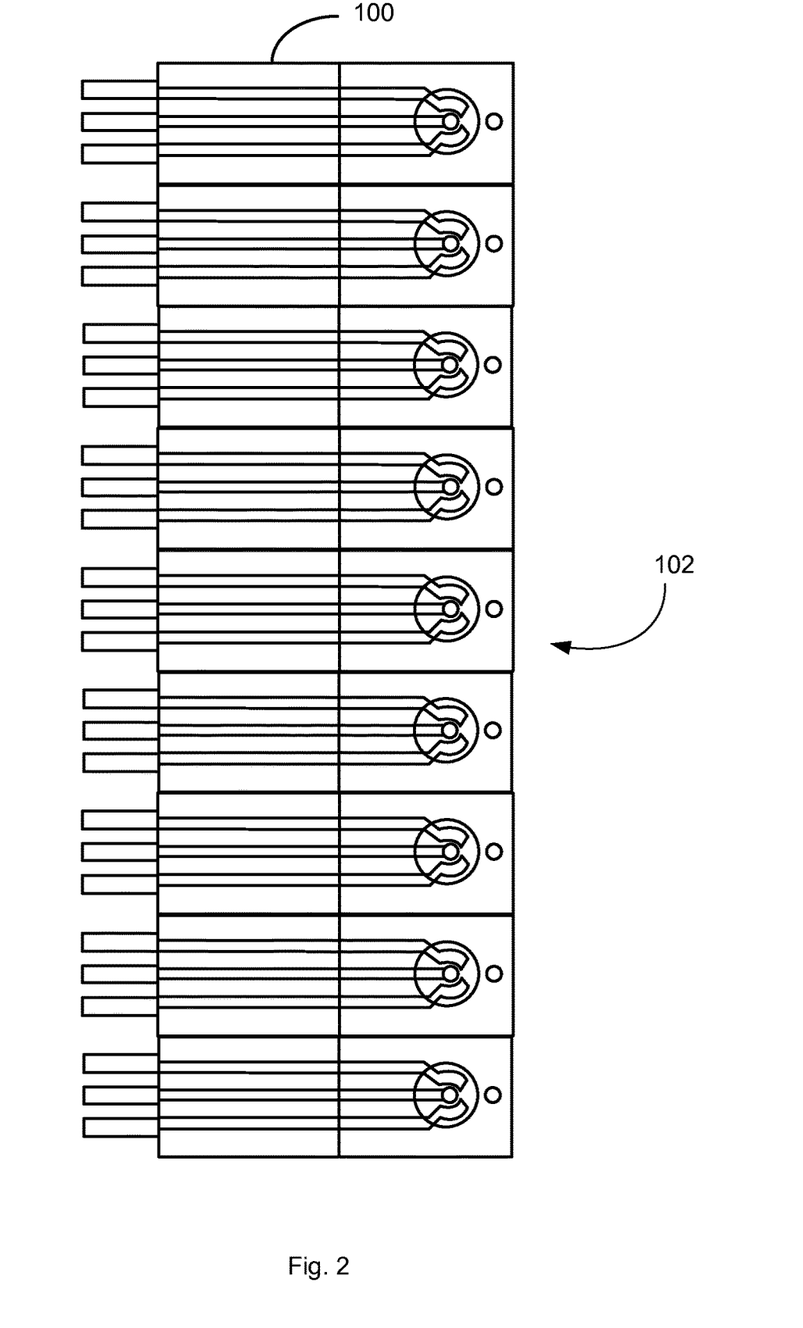
FIG. 2 is a top plan view of an array of biosensors manufactured by a screen-printing process.

The biosensor illustrated in FIGS. 1 and 2 can be fabricated on a substrate 100 formed from polyester or other electrically non-conductive material, such as other polymeric materials, alumina ($Al_2O_3$), ceramic based materials, glass or a semi-conductive substrate, such as silicon, silicon oxide and other covered substrates. Multiple sensor devices 102 can thus be formed on a common substrate 100 (FIG. 2).

As will be appreciated, variations in the geometry and size of the electrodes are contemplated.

The biosensor can be made using a thin film, thick film, and/or ink-jet printing technique, especially for the deposition of multiple electrodes on a substrate. The thin film process can include physical or chemical vapor deposition. Electrochemical sensors and thick film techniques for their fabrication are discussed in U.S. Pat. No. 4,571,292 to C. C. Liu et al., U.S. Pat. No. 4,655,880 to C. C. Liu, and co-pending application U.S. Ser. No. 09/466,865, which patents and application are incorporated by reference in their entirety. By way of example, in the case of the carbon electrodes, active carbon is mixed with a binder, deposited like an ink on the substrate, and allowed to dry.

The voltage source can apply a voltage potential to the working electrode and reference and/or counter electrode, depending on the design of the biosensor. The current between the working electrode and counter electrode can be measured with a measuring device or meter. Such current is due to the reduction occurring at the working electrode of $H_2O_2$ generated by LOXL2 in bodily fluid that is combined with the reaction solution.

The amount or level of current measured is proportional to the amount of $H_2O_2$ generated and the level or amount of LOXL2 in the bodily fluid as well as the risk or presence of breast cancer in the subject. Once the current level generated by the bodily fluid tested with the biosensor is determined, the level can be compared to a predetermined value or control value to provide information for diagnosing or monitoring of breast cancer in a subject. For example, the current level can be compared to a predetermined value or control value to determine if a subject is afflicted with or has breast cancer. An increased current level compared to a predetermined value or control value can be indicative of the subject having breast cancer; whereas similar or decreased current level compared to a predetermined value or control value can be indicative of the absence of breast cancer in the subject.

The current level generated by the bodily fluid obtained from the subject can be compared to a current level of a bodily fluid previously obtained from the subject, such as prior to administration of a therapeutic. Accordingly, the methods described herein can be used to measure the efficacy of a therapeutic regimen for the treatment of breast cancer in a subject by comparing the current level obtained before and after a therapeutic regimen. Additionally, the methods described herein can be used to measure the progression of breast cancer in a subject by comparing the current level in a bodily fluid obtained over a given time period, such as days, weeks, months, or years.

The current level generated by a bodily fluid of the subject may also be compared to a predetermined value or control value to provide information for determining the severity or aggressiveness of the breast cancer in the subject. Thus, in some aspect, the current level may be compared to control values obtained from subjects with well known clinical categorizations, or stages, of histopathologies related to breast cancer (e.g., invasive and metastatic versus non-invasive breast cancer). In one particular embodiment, the current in a sample can provide information for determining the metastasis and disease progression of late-stage and poorly differentiated triple-negative breast cancer (TNBCs) in the subject.

A predetermined value or control value can be based upon the current level in comparable samples obtained from a healthy or normal subject or the general population or from a select population of control subjects. In some aspects, the select population of control subjects can include individuals diagnosed with breast cancer. For example, a subject having a greater current level compared to a control value may be indicative of the subject having a more advanced stage of a breast cancer or a more invasive category of breast cancer.

The select population of control subjects may also include subjects afflicted with breast cancer in order to distinguish subjects afflicted with breast cancer from those with benign breast disease. In some aspects, the select population of control subjects may include a group of individuals afflicted with breast cancer.

The predetermined value can take a variety of forms. The predetermined value can be a single cut-off value, such as a median or mean. The predetermined value can be established based upon comparative groups such as where the current level in one defined group is double the current level in another defined group. The predetermined value can be a range, for example, where the general subject population is divided equally (or unequally) into groups, or into quadrants, the lowest quadrant being subjects with the lowest current level, the highest quadrant being individuals with the highest current level. In an exemplary embodiment, two cutoff values are selected to minimize the rate of false positive and negative results.

In another aspect, the present invention provides kits comprising materials useful for carrying out diagnostic methods according to the present invention. The systems, assays and detection procedures described herein may be performed by diagnostic laboratories, experimental laboratories, or practitioners. The invention provides kits, which can be used in these different settings.

Materials and reagents for detecting LOXL2 in a bodily sample, detecting breast cancer, and/or assessing the severity of breast cancer in a patient according to the inventive methods may be assembled together in a kit. In certain aspects, an inventive kit comprises a reaction solution that quantitatively detects levels of LOXL2, and instructions for using the kit according to a method of the invention. Each kit may preferably include a reaction solution for generating $H_2O_2$ upon combination with LOXL2. Thus, for detecting/quantifying LOXL2 in a bodily sample, the reaction solution may include lysine and distilled $H_2O$ to generate $H_2O_2$ upon combination with LOXL2. A kit of the present invention may further include a biosensor described herein for determining the level of generated $H_2O_2$.

Depending on the procedure, the kit may further comprise one or more of, extraction buffer and/or reagents, and dilution buffers. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer, solution and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain aspects, the kits of the present invention further include control samples. For example, control samples may include solutions having specific concentrations of LOXL2 correlating to the level of LOXL2 in a subject with breast cancer, a particular subtype and/or stage of breast cancer or clinical outcome. Control samples for use in the kits can also include negative control samples. In some aspects the kits may include a stock solution of LOXL2 for preparing solutions having desired concentrations of LOXL2 for use in the described methods. For example varying concentrations of LOXL2 can be used to create a biosensor calibration curve as described herein.

Instructions for using the kit, according to one or more methods of the invention, may comprise instructions for processing the biological sample obtained from the subject, and/or for performing the test, instructions for interpreting the results. As well as a notice in the form prescribed by a governmental agency (e.g., FDA) regulating the manufacture, use or sale of pharmaceuticals or biological products.

The Example that follows illustrates embodiments of the present invention and are not limiting of the specification and claims in any way.

Example 1

In this Example, we present the results of the development of a reaction solution and biosensor for the detection of LOXL2 in human serum and urine samples. We first tested our biosensor for the ability to detect levels of LOXL2 in whole blood and identify tumor free mice from those with mammary tumors with breast cancer. We found, using this reaction solution and biosensor with whole blood samples taken from mice that we were able to distinguish, with 100% accuracy, between both tumor-free and mice with 4T1 tumors. Next, we also tested our biosensor for the ability to detect levels of LOXL2 in human serum, plasma and urine samples taken from 10 breast cancer patients and 10 negative control subjects. Similar to the findings in mouse whole blood, we found a striking linear relationship between LOXL2 concentrations and the biosensor measurements where higher levels of LOXL2 from the biological fluids of breast cancer patients as compared to their case control counterparts was observed. These data illustrate that this detection technique was an accurate method for measuring LOXL2 in biological fluids obtained from breast cancer patients without the need to subject them to a complicated biopsy process.

Methods

In-Situ Generation of Allysine and its Derivatives

Potential Interference Study of Allysine and Others

As shown in scheme 1, the formation of an aldehydic-lysine compound from lysine was catalyzed by LOXL2, generating the reaction co-products $NH_3$, $H_2O_2$ and allysine. It was necessary to validate that allysine, $NH_3$ (in fact $NH_4OH$ in the aqueous testing medium), and reactant lysine would not interfere with the electrochemical detection. This verification was accomplished by carrying out the cyclic voltammetric studies of allysine, $NH_4OH$ and lysine ensuring that no oxidation current was produced that could interfere with the $H_2O_2$ oxidation.

Allysine is not commercially available, so we first carried out in-situ generation of allysine and its derivatives ensuring that they will not interfere with the electrochemical oxidation of $H_2O_2$ generated. Commercially available L-allysine ethylene acetal (#215054-80-1, Sigma-Aldrich, St. Louis, Mo.) was hydrolyzed at room temperature with hydrochloric acid (HCl; #258148, Sigma-Aldrich) in tetrahydrofuran (THF; #494461, Sigma-Aldrich) to generate allysine in situ according to the reaction scheme below.

l-allysine ethylene acetal l-allysine

Briefly, one milliliter of 1 M HCl was added to 4.0 mL of tetrahydrofuran containing L-allysine ethylene acetal (0.264 mmol). The solution was stirred at room temperature under argon atmosphere for 1.25 hr, and then the reactions were neutralized with NaOH (#221465, Sigma-Aldrich) under argon. Afterward, 100 μL aliquots were extracted every 10 min throughout the reaction and tested with 2,4-Dinitrophenylhydrazine (2,4-DNP; #D199303, Sigma-Aldrich) for the presence of aldehyde. As early as 10 min into the reaction, the presence of aldehyde was detected using the 2,4-DNP test. On the other hand, ninhydrin (#N7285, Sigma-Aldrich) was used to confirm the presence of the amino acid moieties. These tests could not confirm the sole presence of allysine. We anticipated the formation of aldol or lysinorleucine derivatives by these rapid condensation reactions (FIG. 4), however, these conversion processes occurred spontaneously so it was only necessary to measure the cyclic voltammograms during the in situ generation of allysine. Hence, a cyclic voltammetry study was performed during the course of the reaction in order to investigate if allysine or its derivatives would contribute to any oxidation current that may interfere with the electrochemical detection of $H_2O_2$. Aliquots were tested at t=0, 10, 20, 30, and 40 min, respectively, throughout the course of the L-allysine ethylene acetal hydrolysis reaction.

LOXL2 Biosensor Fabrication

Gold film was vapor deposited onto 12 mil (0.0030 mm) thick polyethylene terephalate (PET) substrate in the dimension of 355×280 mm², and the gold film was sputtering deposited about 1000 Å in thickness. Consequently, the electrode elements were very uniform and reproducible. The cost of each substrate was relatively low, and 100 biosensor prototypes in four rows were produced on each substrate making the biosensor cost-effective. The biosensor had a three-electrode configuration of working, counter and reference electrodes. Both the working and the counter electrodes were gold and defined by laser etching technique yielding the desired structure and dimensions. The reference electrode was Ag/AgCl and printed with DuPont #5870 Ag/AgCl thick film ink, while the remaining electrical connectors were silver and printed with DuPont #5025 silver ink. The insulation layer was also thick-film printed using Nazdar SPL 34 silicone-free dielectric ink. The overall size of each individual sensor was 33.0×8.0 mm², and the working gold electrode was approximately 1.54 mm² with a diameter of 1.4 mm. This biosensor could accommodate 10 μl of test sample.

LOXL2 Biosensor Calibration and Testing Procedure

Typically, lysine solution was prepared by dissolving 10 mg of lysine powder in 1 mL of distilled water, which was subsequently diluted to a working concentration of 680 nM. In a typical run, specific concentrations of 60, 120, 180 nM of human LOXL2 (catalog #SRP0179, Sigma-Aldrich) were prepared from a 3 μM LOXL2 solution. The calibration curve for the LOXL2 was established using a total volume of 50 μL of mixed solution of 680 nM lysine solution and the specific LOXL2 concentration solution. This mixed solution was then incubated for 400 seconds at room temperature, at which point 10 μL of the reaction mixture was placed on the surface of the biosensor for amperometric measurements. The oxidation current output of the $H_2O_2$ was used to correlate with the LOXL2 concentrations. All measurements were conducted at room temperature, and at least 3 separate measurements were repeated for each LOXL2 concentration. For the detection of LOXL2 in murine and human biological fluids, namely, serum and urine samples, identical process to the calibration step described above was used, and the testing procedure of these biological samples was: A 50 μL of 680 nM lysine solution was first placed in a small tube for handling and 5 μL of the murine or human sample was then added and incubated for 400 seconds. Then 10 μL of the incubated test solution was placed on top of the working electrode for measurement.

Collection of the Mouse Blood Samples

Murine metastatic 4T1 breast cancer cells were engineered to stably express luciferase by transfection with pNifty-CMV-luciferase, followed by Zeocin-mediated antibiotic selection (500 μg/ml). Mammary tumor development was initiated by engrafting 4T1 cells (1×10⁴ cells) onto the mammary fat pad of 4-week old Balb/C mice. The development and progression of 4T1 tumors was monitored by intravital bioluminescent imaging of the animals on a Xenogen IVIS-200 (Caliper Life Sciences, Hopkinton, Mass., USA) as described. Upon completion of the studies, the tumor-free and 4T1 tumor-bearing mice were euthanized and whole-blood was immediately collected via the superior vena cava and supplemented with 0.32% sodium citrate prior to storage at −80° C. Samples were thawed and applied to the biosensor to monitor LOXL2 levels as described above.

Collection of the Human Blood and Urine Samples

Samples from breast cancer patients and healthy controls were obtained from a subset of patients participating in a larger breast cancer case-control study. Breast cancer patients were recruited from all newly diagnosed breast cancer patients seen at University Hospitals Case Medical Center (UHCMC, Cleveland, Ohio) and its affiliated clinics. Controls were recruited from patients receiving normal mammograms at the mammography centers of UHCMC.

Blood and urine samples were collected from both patients and controls, and were collected from patients prior to the initiation of radiation therapy or chemotherapy. Serum and plasma were isolated the same day of collection, and all serum, plasma and urine specimens were stored in −80° C. until analyzed. For LOXL2 measurements serum, plasma and urine from 10 patient and 10 control samples were randomly selected. Samples were thawed and then placed onto the sensor using the aforementioned reactions conditions.

Results

Chemistry and Construction of the LOXL2 Biosensor

LOXL2 is a member of the LOX family, which catalyzes oxidative deamination of δ-amino group of lysine, resulting in the conversion of peptidyl lysine to peptidyl-α-amino-adipic-δ-semialdehyde (allysine) and the release of stoichiometric quantities of ammonia and hydrogen peroxide ($H_2O_2$). Therefore, it is possible to develop a method to quantitatively determine the levels of $H_2O_2$ produced by this peptidyl lysine reaction, and thus to provide a means to assess the relative expression levels of LOXL2 in human biological fluids. Consequently, monitoring of LOXL2 levels will identify women harboring undetected breast disease, and will also provide an assessment of the stage and likelihood for metastasis by these mammary tumors. An important consideration in exploiting this chemistry lies in verifying that the reactant lysine, as well as its co-products allysine and $NH_3$ do not interfere with the production and detection of $H_2O_2$.

The biosensor was fabricated by sputtering a gold film onto a polyethylene terephalate (PET) substrate which was 355×280 mm². This deposition resulted in the production of a highly uniform gold film. Laser etching was employed to define the gold working and counter electrodes, while the Ag/AgCl reference electrode, the insulation layer, and the electrical connecting parts were printed using a thick-film printing technique. Our combined techniques resulted in the well-defined, reproducible, and cost-effective production of 4 rows of 100 biosensor prototypes on each substrate. The overall dimensions of an individual biosensor were 33.0×8.0 mm² and comprised a three-electrode configuration of the counter, reference, and working electrodes. Each individual biosensor was approximately 1.54 mm² with a diameter of 1.4 mm, which was sufficient to accommodate a 10 μL sample volume.

The oxidation current of $H_2O_2$ produced electrochemically could quantify the LOXL2. The oxidation of $H_2O_2$ occurred at the surface of the working electrode at an applied potential of +0.4 volt versus the Ag/AgCl reference electrode. An Electrochemical Workstation, CHI 660 Model A or B (CH Instruments Inc. Houston, Tex.) supplied this applied potential.

Figure 3A:
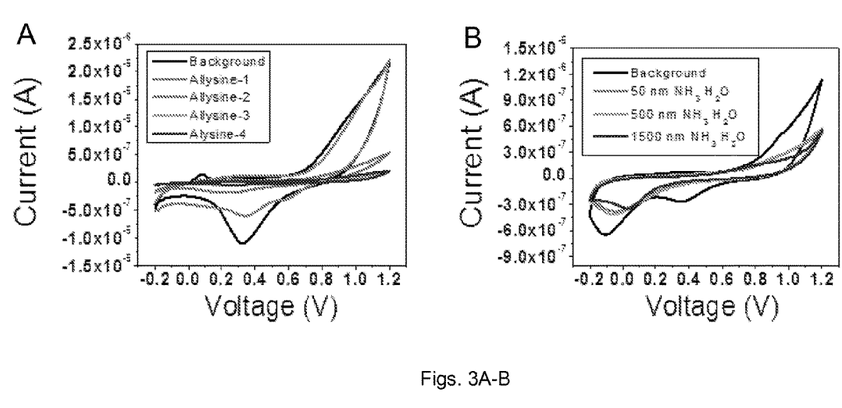

As shown in scheme 1, the formation of an aldehydic-lysine compound from lysine was catalyzed by LOXL2, generating the reaction co-products $NH_3$, $H_2O_2$ and allysine. It was necessary to validate that allysine, $NH_3$ (in fact $NH_4OH$ in the aqueous testing medium), and reactant lysine would not interfere with the electrochemical detection. This verification was accomplished by carrying out the cyclic voltammetric studies of allysine, $NH_4OH$ and lysine ensuring that no oxidation current was produced that could interfere with the $H_2O_2$ oxidation. FIGS. 3A and 3B show the cyclic voltammograms of allysine and $NH_4OH$, respectively. Allysine is not commercially available, and as such, a chemical hydrolysis reaction using commercially available L-allysine ethylene acetal to produce allysine in situ was needed. The generated reactive allysine moieties reacted further with either itself to produce allysine aldol, or with excess lysine to yield lysinonorleucine. These reactions occurred spontaneously, and it was only necessary to measure the cyclic voltammogram during the in situ generation of allysine. This would ensure its inability to produce any $H_2O_2$, or to generate any unwanted oxidation current. FIG. 3A shows that the resultant accumulation of allysine, in the presence of tetrahydrofuran (THF) and HCl did not contribute to the measured oxidation current of $H_2O_2$. FIG. 3B shows that $NH_4OH$ also did not contribute to the oxidation current of $H_2O_2$, nor did lysine until catalytically-active LOXL2 was added to the reaction mixtures. This was shown in the background measurement in FIG. 4.

Calibration of the LOXL2 Biosensor

Figure 4:
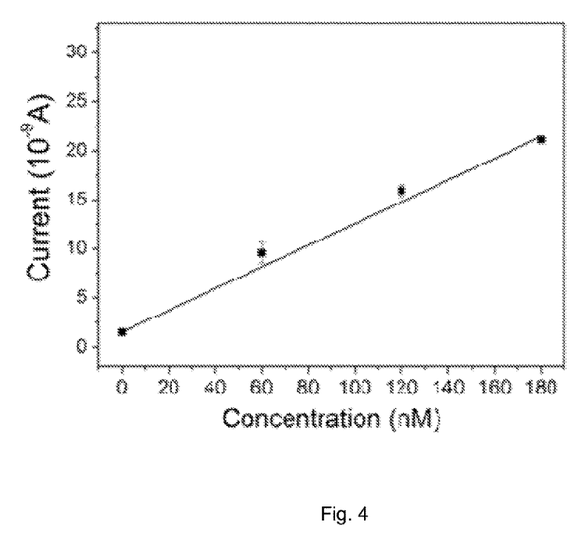
FIG. 4 illustrates a plot showing the calibration of a LOXL2 biosensor in accordance with an aspect of the application. The calibration curve of current output versus the LOXL2 concentration covering 0-180 nM. The data were analyzed using an ordinary least squares fit of a simple linear regression model and are the mean±SD (n=3).

After validating that the reactants and co-products did not generate any considerable oxidation currents during the detection of $H_2O_2$ from the enzymatic reaction of LOXL2 reacting with lysine, the biosensor was calibrated to determine its sensitivity to detect the $H_2O_2$ produced by the LOXL2 based on the reaction mechanism illustrated in reaction scheme 1. Amperometric measurements were performed by determining the oxidation current of $H_2O_2$ as a means to quantify the level of LOXL2 present. A calibration curve between the biosensor current output and the $H_2O_2$ concentration in deionized water was established ensuring that any $H_2O_2$ generated can be used to quantify LOXL2 by the biosensor. In doing so, we mixed known quantities of the substrate, lysine (680 nM) with LOXL2 to produce $H_2O_2$ which was electrochemically oxidized. The oxidation current was then used to quantify levels of LOXL2 in the test samples. For these calibration experiments, the currents produced over the concentration range of 60-180 nM LOXL2 were monitored. The reaction was incubated for 400 seconds prior to placing it on the biosensor for amperometric measurement. FIG. 4 shows the calibration curve of LOXL2, which exhibited an outstanding linear relationship with the measured current showing a coefficient of determination of 0.997, and excellent consistency between replicates (n=3).

Detection of LOXL2 Activity in Murine and Human Biological Fluids

Figure 5A:
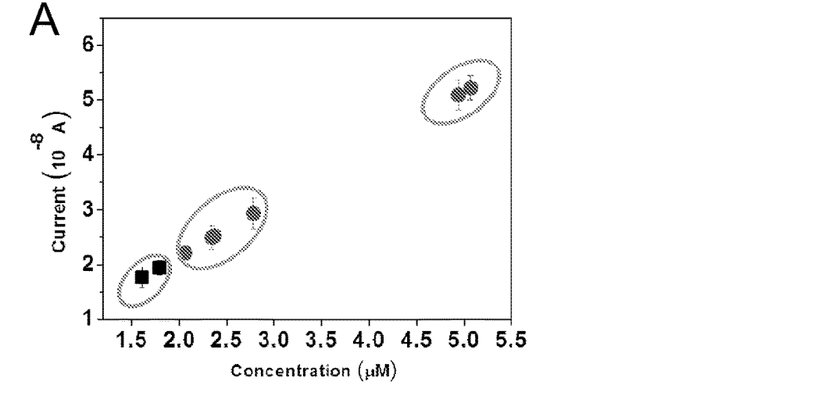
Figure 5B:
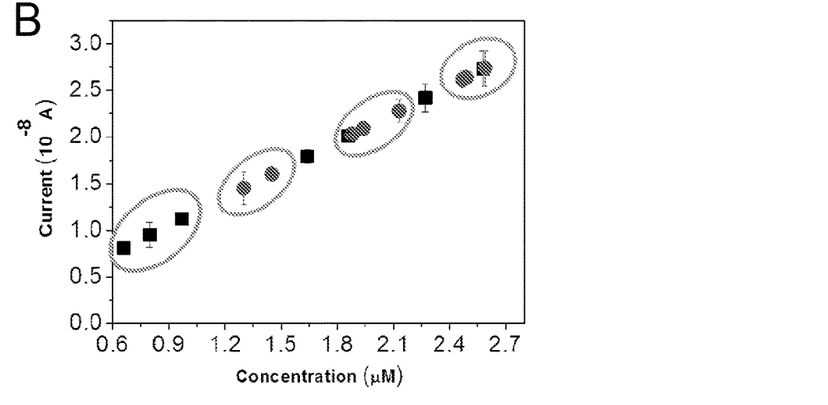
Figure 5C:
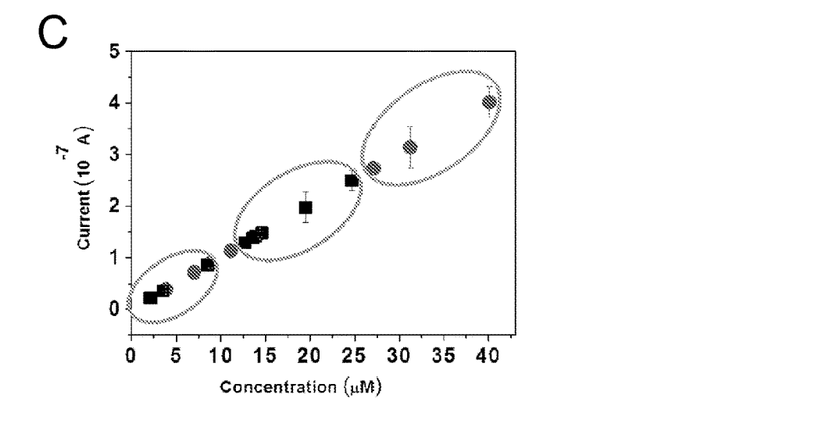

To test the practical application of this LOXL2 biosensor, measurement of the level of LOXL2 in murine and human biological specimens was carried out. FIG. 5A shows the levels of LOXL2 detected in the mouse whole blood samples obtained from control and 4T1 mammary tumor-bearing mice. The control sample showed a lower LOXL2 concentration, as was expected. Indeed, the electrochemical biosensor clearly distinguished the mice bearing 4T1 mammary tumors from those that were tumor-free (FIG. 5A). Similarly, our novel biosensor clearly detected LOXL2 in specimens of human serum (FIG. 5B), plasma (data not shown), and urine (FIG. 5C). There was a striking linear relationship between LOXL2 concentrations and the biosensor measurements, illustrating that this detection technique was an accurate method for measuring LOXL2 in biological fluids obtained from breast cancer patients without the need to subject them to a complicated biopsy process. There was a trend showing that higher levels of LOXL2 from the biological fluids of breast cancer patients as compared to their case control counterparts (FIGS. 5B, C). These findings collectively demonstrated the construction and successful implementation of an electrochemical LOXL2 biosensor as a rapid, sensitive, and noninvasive method for the quantification of LOXL2 in breast cancer patients.

Figure 6:
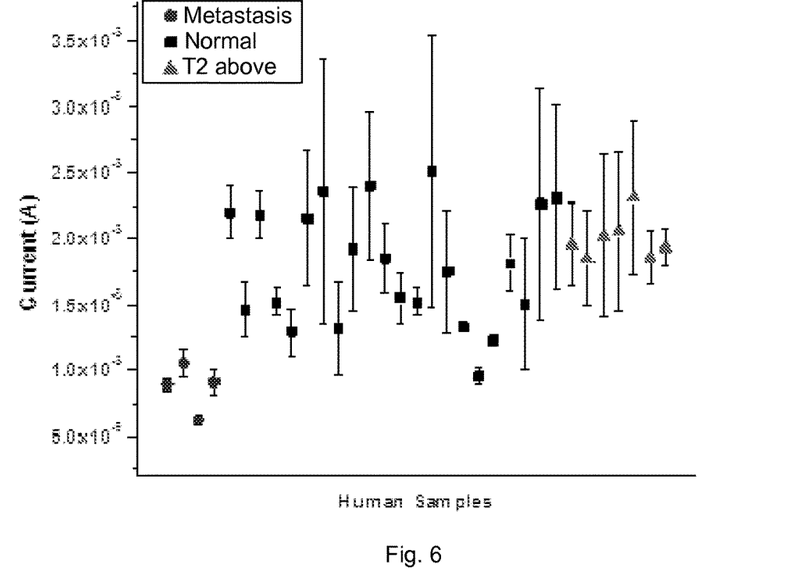
FIG. 6 illustrates a graph showing the test results of a total of 30 patient blood samples and four control samples. It was clearly shown that the LOXL2 levels in the blood samples of the breast cancer patients were higher than those of control samples.
Figure 7:
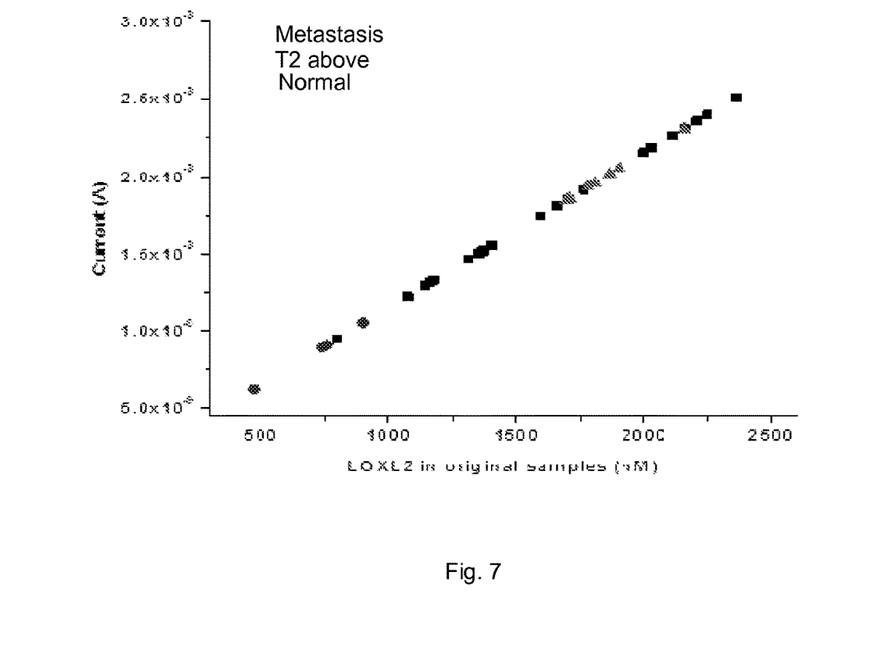
FIG. 7 illustrates a plot showing the current outputs of the blood samples from the breast cancer patients and control collected in Hospital of Hope in San Diego, Calif.
Figure 8:
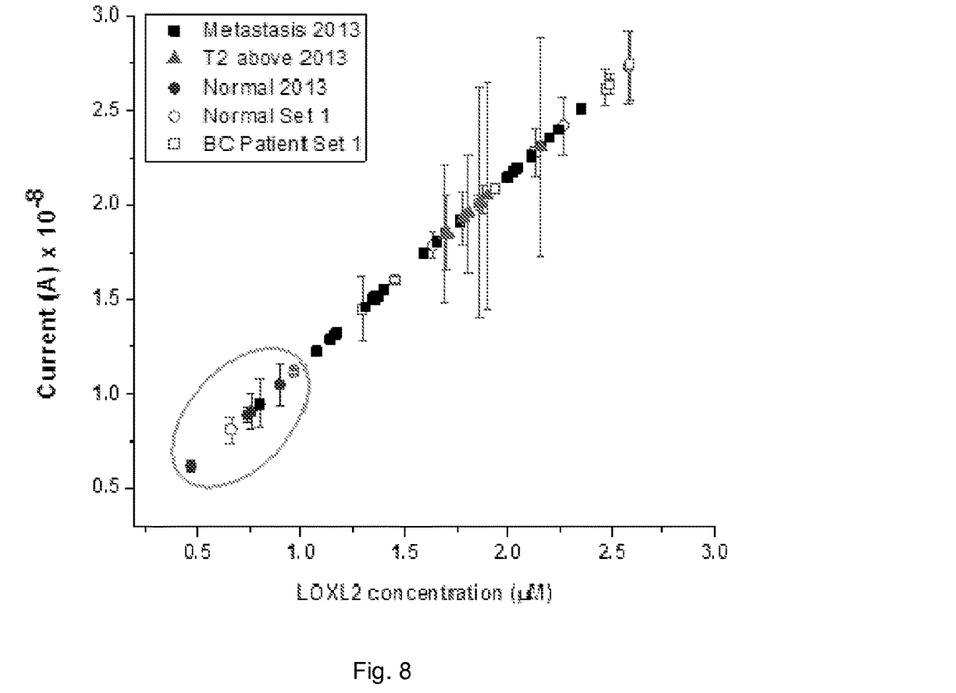
FIG. 8 illustrates a plot showing the combined testing results of the blood samples of breast cancer patients from different sources and reflects the same trend: same order of magnitude of the LOXL2 levels in breast cancer patients and control samples.

FIG. 6 shows the test results of a total of 30 patient blood samples and four control samples. It was clearly shown that the LOXL2 levels in the blood samples of the breast cancer patients were higher than those of control samples. FIG. 7 shows the current outputs of the blood samples from the breast cancer patients and control collected in Hospital of Hope in San Diego, Calif. More importantly, FIG. 8 shows the combined testing results of the blood samples of breast cancer patients from different sources and reflects the same trend: same order of magnitude of the LOXL2 levels in breast cancer patients and control samples.

Inhibition Study of LOXL2 Levels in Mouse Blood Samples

Figure 9:
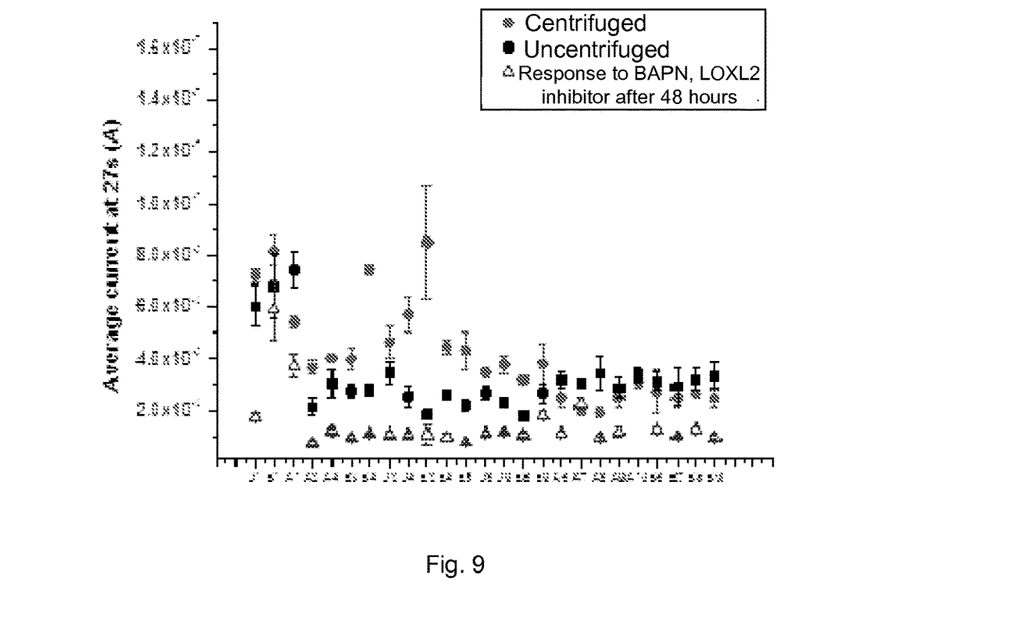
FIG. 9 illustrates a plot showing inhibition study of LOXL2 in mouse blood samples using BAPN as the inhibitor.

In order to ensure the biosensor detects LOXL2, an inhibition study of LOXL 2 was carried out using 24 mouse blood samples. β-aminopropionitrile (βAPN) was used in this study. Typically, 10 µL of 2 mM BAPN was added into 5 µL of mouse blood samples. A 48 hours of incubation time was chosen based on the results of the studies of various incubation time. After that, 40 µL of 680 nM lysine solution was added and incubated for 400 seconds, similar to the process described above. The current outputs were recorded at 27 seconds. FIG. 9 shows the results of the current outputs obtained from whole blood or their clarified counterparts (i.e., centrifuged at 800 rpm for 30 minutes) incubated with or without βAPN. Each blood sample was measured in triplicate. It was obvious that LOXL 2 was inhibited by the βAPN, thereby ensuring that this biosensor protoype measured LOXL2 as the mechanism suggested.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention the following is claimed:

1. A method of detecting lysyl oxidase-like 2 protein (LOXL2) levels in a subject, the method comprising:
    obtaining a bodily sample from the subject, the bodily sample comprising a bodily fluid selected from the group consisting of blood, plasma, sera, and urine,
    combining the bodily sample with at least one reaction solution for generating $H_2O_2$ upon combination with LOXL2 in the bodily sample, the reaction solution including dissolved lysine powder as substrate that can be oxidatively deaminated by LOXL2 to generate α-aminoadipic-δ-semialdehyde (allysine) and hydrogen peroxide ($H_2O_2$); and
    detecting electrochemically the amount of $H_2O_2$ generated in the reaction solution with a biosensor, wherein increased amount of $H_2O_2$ detected compared to a control is indicative of an increased amount of LOXL2 in the bodily sample, and
    wherein the biosensor includes a working electrode, a counter electrode and a reference electrode.

2. The method of claim 1, the working electrode and counter electrode including catalyst particles for increasing the rate of electrochemical oxidation-reduction reaction with $H_2O_2$ and providing the detection of $H_2O_2$ at a lower oxidation potential than without the presence of the catalyst particles.

3. The method of claim 2, the catalyst particles comprising nano-particle metallic catalysts.

4. The method of claim 2, the catalyst particles comprising a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb.

5. The method of claim 2, the catalyst particles comprising iridium oxide particles.

6. The method of claim 1, further comprising applying voltage potentials to the working electrode and counter electrode and measuring the current flow between the working electrode and counter electrode to determine the level of $H_2O_2$.

7. A method of detecting breast cancer or an increased risk of breast cancer in a subject, the method comprising:
    obtaining a bodily sample from the subject, the bodily sample comprising a bodily fluid selected from the group consisting of blood, plasma, sera, and urine,
    combining the bodily sample with at least one reaction solution for generating $H_2O_2$ upon combination with LOXL2 in the bodily sample, the reaction solution including dissolved lysine powder as substrate that can be oxidatively deaminated by LOXL2 to generate α-aminoadipic-δ-semialdehyde (allysine) and hydrogen peroxide ($H_2O_2$); and
    detecting electrochemically the amount of $H_2O_2$ generated in the reaction solution with a biosensor, wherein increased amount of $H_2O_2$ detected compared to a control is indicative of the subject having breast cancer or an increase risk of breast cancer, and
    wherein the biosensor includes a working electrode, a counter electrode and a reference electrode.

8. The method of claim 7, the working electrode and counter electrode including catalyst particles for increasing the rate of electrochemical oxidation-reduction reaction with $H_2O_2$ and providing the detection of $H_2O_2$ at a lower oxidation potential than without the presence of the catalyst particles.

9. The method of claim 8, the catalyst particles comprising nano-particle metallic catalysts.

10. The method of claim 8, the catalyst particles comprising a unary metal (M), a binary metal (M-X), a unary metal oxide (MOy), a binary metal oxide (MOy-XOy), a metal-metal oxide composite material (M-MOy) or a combination of which, wherein y is less than 3, and M and X are independently selected from a group consisting of Li, Na, Mg, Al, K, Ca, Cr, Mn, Fe, Co, Ni, Cu, Zn, Ga, Sr, Y, Zr, Nb, Mo, Ru, Rh, Pd, Ag, Cd, In, Sn, Ba, La, Ce, Pr, Nd, Sm, Eu, Gd, Tb, Dy, Ho, Er, Tm, Lu, Ta, W, Os, Ir, Pt, Au, and Pb.

11. The method of claim 8, the catalyst particles comprising iridium oxide particles.

12. The method of claim 7, further comprising applying voltage potentials to the working electrode and counter electrode and measuring the current flow between the working electrode and counter electrode to determine the level of $H_2O_2$.

* * * * *